(12) United States Patent
Nedergaard

(10) Patent No.: US 7,250,394 B2
(45) Date of Patent: Jul. 31, 2007

(54) TREATMENT OF GLIAL TUMORS WITH GLUTAMATE ANTAGONISTS

(76) Inventor: Maiken Nedergaard, 7 Hillcrest Ct., South Salem, NY (US) 10590

( * ) Notice: Subject to any disclaimer, the term of this patent is extended or adjusted under 35 U.S.C. 154(b) by 492 days.

(21) Appl. No.: 10/225,396

(22) Filed: Aug. 20, 2002

(65) Prior Publication Data
US 2003/0050224 A1    Mar. 13, 2003

Related U.S. Application Data

(60) Provisional application No. 60/313,030, filed on Aug. 20, 2001.

(51) Int. Cl.
*A01N 37/18* (2006.01)
(52) U.S. Cl. .......................................................... 514/2
(58) Field of Classification Search .............. 514/2–12; 424/130.1–156
See application file for complete search history.

(56) References Cited

U.S. PATENT DOCUMENTS

| | | |
|---|---|---|
| 4,122,193 A | 10/1978 | Scherm et al. |
| 5,622,952 A | 4/1997 | Weber et al. |
| 5,776,935 A | 7/1998 | Danysz et al. |
| 5,830,998 A | 11/1998 | Maccecchini |
| 6,071,970 A | 6/2000 | Mueller et al. |
| 6,180,613 B1 | 1/2001 | Kaplitt et al. |
| 6,197,820 B1 | 3/2001 | Sontheimer et al. |

FOREIGN PATENT DOCUMENTS

| | | |
|---|---|---|
| EP | 1 002 535 A1 | 5/2000 |
| WO | WO 00/24395 | 5/2000 |
| WO | WO 00/62771 | 10/2000 |

OTHER PUBLICATIONS

Lipton SA (NeuroRx®: The Journal of American Society for Experimental NeuroTherapeutics 2004;1(1):101-110.*
Groothius DR Neuro-Oncology 2000;2:45-59.*
http://www.ncbi.nlm.nih.gov/entrez/query.fcgi?cmd=Retrieve&db=mesh&list_uids=68008527&dopt=Full.*
Rubin et al (Pathology 2nd Edition, 1994, J.B. Lippincott Company, Philadelphia, pp. 1437-1438).*
Rzeski et al., "Glutamate Antagonists Limit Tumor Growth," *PNAS* 98(11):6372-6377 (2001).
Takano et al., "Glutamate Release Promotes Growth of Malignant Gliomas," *Nature Med.* 7:1010-1015 (2001).
Hesselink et al., "The Role of Probenecid-Sensitive Organic Acid Transport in the Pharmacokinetics of N-Methyl-D-Aspartate Receptor Antagonists Acting at the Glycine$_B$- Site: Microdialysis and Maximum Electroshock Seizures Studies," *J. Pharmacol. Exp. Ther.* 290(2):543-550 (1999).
Takano et al., "Glutamate Release Promotes Growth of Malignant Gliomas," *Nature Medicine* 7(9):1-6 (2001).
Smith et al., "Autoimmune Encephalomyelitis Ameliorated by AMPA Antagonists," *Nature Medicine* 6(1):62-66 (2000).
Meldrum, "Glutamate and Glutamine in the Brain. Glutamate as a Neurotransmitter in the Brain: Review of Physiology and Pathology," *American Society for Nutritional Sciences* (Supp.) 1007S-1015S (2000).
Lee et al., "The Changing Landscape of Ischaemic Brain Injury Mechanisms," *Nature* 399(Supp.):A7-A14 (1999).
Ye et al., "Glioma Cells Release Excitotoxic Concentrations of Glutamate," *Cancer Research* 59:4383-4391 (1999).

* cited by examiner

*Primary Examiner*—Christopher H. Yaen
(74) *Attorney, Agent, or Firm*—Nixon Peabody LLP

(57) ABSTRACT

The present invention relates to a method of treating glial tumors in a subject, which includes providing a glutamate antagonist or a NMDA receptor antagonist and administering the glutamate antagonist or NMDA receptor antagonist to a subject with a glial tumor of the brain or spinal cord under conditions effective to treat the glial tumor.

11 Claims, 6 Drawing Sheets

TREATMENT OF GLIAL TUMORS WITH GLUTAMATE ANTAGONISTS

The present application claims benefit of U.S. Provisional Patent Application Serial No. 60/313,030, filed Aug. 20, 2001.

The subject matter of this application was made with support from the United States Government under grant numbers NS30007 and NS38073. The United States Government may have certain rights.

FIELD OF THE INVENTION

The present invention relates to the treatment of glial tumors in a living system by administering glutamate antagonists that modulate glutamate excitatory neurotransmitter function at ionotropic glutamate receptor complexes.

BACKGROUND OF THE INVENTION

Despite significant improvements in the early detection of malignant gliomas, the median survival of patients remains less than 12 months from the time of diagnosis (Benedetti et al., "Gene Therapy of Experimental Brain Tumors Using Neural Progenitor Cells," *Nature Med.*, 6:447–450 (2000); Russell et al., *Pathology of Tumors of the Nervous System*, (Arnold, Ed.), London (1989)). Malignant gliomas rarely metastasize outside the central nervous system, but they will diffusely invade the host brain. Peritumor brain tissue shows various types of inflammatory responses, including activated macrophages and microglia, hypertrophic reactive astrocytes, vascular invasion and edema formation (Schiffer, D., "Brain Tumors. Biology, Pathology, and Clinical References" Springer, New York, Berlin, Heidelberg (1997)). Neurons are preserved in the immediate vicinity of some tumors, but other tumors are surrounded by degenerating neurons, progressing to neuronal loss (Id). Variability in the local presentation of resident neurons has been a frequent but unexplained observation in tumor neuropathology. A similar variable observation has been the incidence of epileptic activity in glioblastoma, which approaches 50% of all cases (Cascino, G., "Epilepsy and Brain Tumors: Implications for Treatment," *Epilepsia*, 31:S37–44 (1990); Pallias, J. E., "A Review of 2,413 Tumours Operated Over a 30-year Period," *J. Neuroadiol.*, 18:79–106 (1991)).

Human glioma cells actively release the excitatory amino acid. glutamate in vitro, and the extracellular levels of glutamate are increased both in and around experimental glioma implants in vivo (Pallias, J. E., "A Review of 2,413 Tumours Operated Over a 30-year Period," *J. Neuroadiol.*, 18:79–106 (1991); Ye et al., "Compromised Glutamate Transport in Human Glioma Cells: Reduction-Mislocalization of Sodium-Dependent Glutamate Transporters and Enhanced Activity of Cystine-Glutamate Exchange," *J. Neurosci.*, 19:10767–10777 (1999); Behrens et al., "Extracellular Glutamate and Other Metabolites in and Around RG2 Rat Glioma: An Intracerebral Microdialysis Study," *J. Neurooncol.*, 47:11–22 (2000)). Glutamate is the principal excitatory transmitter within the vertebrate nervous system. Approximately 40% of all synaptic terminals release glutamate, and glutamate mediates many physiological functions by activation of different receptor types (Watkins and Evans, "Excitatory Amino Acid Transmitters," *Annu. Rev. Pharmacol.*, 21:165–189). Two main categories of glutamate receptors have been identified, including ionotropic glutamate receptors and metabotropic glutamate receptors. Ionotropic glutamate receptors can be subdivided into N-methyl-D-aspartate (NMDA), a-amino-3-hydroxy-5-methyl-4-isoxazole-propionate (AMPA), and kainate receptors.

There is considerable experimental and clinical evidence indicating that glutamate is involved in the pathogenesis of neuronal degeneration in the context of hypoxia/ischemia and trauma of the central nervous system, seizures and hypoglycemia. In addition, glutamate is thought to be involved in the pathogenesis of chronic neurodegenerative disorders, such as amyotrophic lateral sclerosis, Huntington's Disease, Alzheimer's Disease, and Parkinson's Disease. Functional glutamate receptors have been identified in lung, muscle, pancreas, and bone (Mason et al., *Bone* 20:199–205 (199); Patton et al., *Bone* 22:645–649 (1998)). Glutamate receptors have also been demonstrated to be involved in the suppression of neuroblastoma cells (European patent application EP1002535A1). However, no link has been established so far between glutamate receptors and glial cell tumors. While recent data show that cultured glioma cells secrete glutamate, the growth potential of glial cell brain tumors has not yet been linked to an excitotoxic mechanism.

Glial tumors, the most prevalent and morbid of which is astrcoytoma and its aggressive derivative glioblastoma multiforme, are the most common cancers of the adult central nervous system. They are also among the least treatable cancers, with a 5 year survival after initial diagnosis of <10% for tumors initially diagnosed at the grade 3 (anaplastic astrocytoma) or 4 (glioblastoma) stages. The currents treatment of glioma and glioblastoma are lacking, and achieve only palliation and short-term increments in survival. They include surgical resection—following which ultimate recurrence rates are over 90%—as well as radiation therapy, and chemotherapies that include cis-platin, BCNU and other mitotic inhibitors. The benefits of these current therapies are brief and temporary, and none are curative (e.g., Schiffer, D. *Brain Tumors. Biology, Pathology, and Clinical References* Springer-Verlag (New York, Berlin, Heidelberg, 1997).

The present invention overcomes the deficiencies in the relevant art.

SUMMARY OF THE INVENTION

The present invention relates to a method of treating glial tumors in a subject. This method involves providing a glutamate antagonist and administering the glutamate antagonist to a subject with a glial tumor under conditions effective to treat the glial tumor.

The present invention also relates to a method of treating glial tumors in a subject which involves providing a NMDA receptor antagonist and administering the NMDA receptor antagonist to a subject with a glial tumor under conditions effective to treat the glial tumor.

The methods of the present invention provide for an improved treatment of glial tumors, a deadly set of cancers that are typically fatal within a year of diagnosis. In accordance with the present invention, glutamate antagonists, which inhibit the excitatory activity of glutamate, are administered in a manner which is effective to slow glial tumor expansion and, therefore, prolong the lives of patients with glial tumors. The methods of the present invention, based upon antagonizing glutamate secretion or its target receptors, demonstrate a new approach for treating brain tumors.

The present invention is directed to the use of glutamate antagonists in suppressing glial tumor expansion, and hence in treating CNS glial tumors, including astrocytoma and glioblastoma, and also their related neural and glial tumors, which include grades 1 and 2 glioma, oligodendroglioma, neurocytoma, dysplastic neuroepithelial tumor, primitive neuroectodermal tumor, and ganglioneuroma. The use of glutamate antagonists in the treatment of systemic cancers has been otherwise proposed for non-brain tumors derived from cells known to be responsive to glutamate (European Patent Application Serial No. 1002535A1 to Ikonomidou, which is hereby incorporated by reference in its entirety). However, the use of glutamate antagonists in brain tumors is not taught or enabled (they studied neuroblastoma, which is derived from the peripheral nervous system, and not from the central nervous system). Further, Ikonomidou does not treat glial cell tumors (a non-metastatic tumor type), let alone does it do so in vivo. Rzeski et al., "Glutamate Antagonists Limit Tumor Growth," *Proc. Nat'l. Acad. Sci. USA* 96(11):6372–77 (2001) extends this observation to the use of glutamate antagonists as cytotoxic agents for a number of cell lines, including breast carcinoma, colon carcinoma, adrenocarcinoma, thyroid carcinoma, rhabdomyosarcoma/medulloblastoma, astrocytoma, and neuroblastoma. In contrast, the present invention specifically teaches the use of glutamate antagonists as a means of suppressing the toxic effects of tumor-derived glutamate on surrounding brain cells. In this context, glutamate antagonists serve to inhibit the spread of tumor cells by preserving normal brain cells which would otherwise be damaged or killed by tumor-derived glutamate (Takano et al., *Nature Med.* 7:1010–15 (2001), which is hereby incorporated by reference in its entirety). This can be accomplished at much lower doses than those at which glutamate antagonists cause direct cytotoxicity (i.e. the mechanism used by Ikonomidou), thereby allowing the therapeutic use of glutamate antagonists at doses which are not associated with systemic toxicity. The present invention hereby teaches the in vivo therapeutic use of glutamate antagonists to treat brain cancer. The present invention takes advantage of the intimate association of normal glial cells with neurons, the glutamate-responsive excitable cell type of the adult brain. By suppressing neuronal activity and glutamate-associated neuronal loss and inflammation, glutamate antagonists may inhibit the spread of glial tumor cells into the affected region of neuronal loss, while concurrently contributing to the local preservation of neuronal viability (Takano et al., *Nature Med.* 7:1010–15 (2001), which is hereby incorporated by reference in its entirety).

BRIEF DESCRIPTION OF THE DRAWINGS

FIG. 1A shows temporal changes of extra-cellular glutamate concentration [Glu], in confluent cultures of C6WT (□), two C6 clones (C6Glu$^+$ (■) and C6Glu$^+$ (●) cells) and primary cortical astrocytes (○). The culture medium initially contained 150 μM glutamate. FIG. 1B shows neuronal cultures were loaded with the calcium indicator fluo-3. Conditioned medium from the C6Glu$^+$, but not from C6Glu$^+$ cells, increased fluo-3 emission. Scale bar, 10 μm FIG. 1C shows C6Glu$^+$ glioma cells secrete neurotoxic levels of glutamate. Relative increase of fluo-3 emission following addition of conditioned medium from C6Glu$^+$ cells , C6Glu$^+$ cells +10 μM MK-801, C6Glu$^+$ cells and astrocytes (■) are compared for percent neuronal death after coculturing for 24 h with C6Glu$^+$ cells, C6Glu$^+$ cells +10 μM MK-801, C6Glu$^+$ cells and astrocytes (■). *, P<0.01; ANOVA. FIG. 1D shows time-lapsed images of a neuronal culture cocultured with C6Glu$^+$ cell aggregates (upper panels) or C6Glu$^+$ cell aggregates (lower panels). Minimal neuronal damage is evident in the coculture with C6Glu$^+$ cells, whereas most neurons are killed within the 14-h observation period by C6Glu$^+$ cells. Scale bar, 50 μm.

FIGS. 2A–C show EAAC1 immunoreactivity in cultured C6Glu$^+$ (FIG. 2A), C6Wt (FIG. 2B), and C6Glu$^+$ cells (FIG. 2C) (left panels). EAAC1 expression was lost in C6Glu$^+$ cells. Glutamate release during a 6-h period in the same clones (right panels). The inhibitor of sodium-dependent glutamate transporters, PDC (◆, 200 μM) reduced glutamate uptake in C6Glu$^+$ cells, but not in C6Glu$^+$ or C6WT cells. Addition of cystine (■, 100 μM), or cystine+S-4CPG (200 μM) had no effect (●, control). FIG. 2D shows glutamate uptake over a 5 min. period (■). Sodium-free solution (■) and PDC (lighter filled square, 100 μM) inhibited uptake of glutamate in C6WT and C6Glu$^+$ cells, but not in C6Glu$^+$ cells. Cystine (□) had no effect.

FIG. 3A shows representative tumors from rates with C6Glu$^+$ (top), C6WT (middle) or C6Glu$^+$ (bottom) cell implants. FIG. 3B shows tumor size 10 d after implantation of cells from C6Glu$^+$, C6WT or C6Glu$^+$ clones. *, P<0.01; **, P<0.001; ANOVA. FIG. 3C shows proliferation rate of C6Glu$^+$ (●), C6WT (■),C6Glu$^+$ (○) cells in culture. FIG. 3D shows relative number of invading C6Glu$^+$, C6WT, C6Glu$^+$ cells in trans-well invasion chamber. FIG. 3E shows Kaplan-Meier survival plot of rats injected with C6Glu$^+$ cells (dotted line, n=13) or C6Glu$^+$ cells (solid line, n=13).

FIG. 4A shows tumor size in MK801- and vehicle-treated rates 10 d after implantation of C6Glu$^+$ cells. FIG. 4B shows proliferation of C6Glu$^+$ glioma cells in presence of 0 (●), 10 (lighter filled circle) or 100 (○) μM MK801. FIGS. 4C and D show glutamate release detected by bioluminescence in brain slices from a rat injected with C6Glu$^+$ (FIG. 4C), C6Glu$^+$ (FIG. 4D) glioma cells 5 d earlier. Top, cresylviolet staining of the C6Glu$^+$ glioma implant. The border of tumor is indicated by arrows. Middle, glutamate-related light production is shown in red and superimposed upon a bright field image of the tumor. Bottom, relative light production within the frame of the picture above. Light production is 2-fold higher in the tumor than compared with normal tissue. In FIG. 4D, glutamate release from the tumor does not differ from surrounding normal brain tissue.

FIG. 5A shows TUNEL cells are dispersed in the surroundings of C6Glu$^+$ (bottom) but not C6Glu$^-$(top) tumors. Sections of a 5-day old implant of C6Glu$^+$ cells were TUNEL stained and counterstained with H&E. Cell identity was examined by double labeling for the neuron-specific antigen MAP2 (fluorescein) and TUNEL (rhodamine). Scale bar, 10 μm. FIG. 5B shows number of TUNEL cells near tumors composed of C6Glu$^-$, C6Glu$^+$ and C6Glu$^+$ cells in rats treated with MK801. FIG. 5C shows numerous ED-1$^+$ microglia infiltrate the tissue surrounding implanted C6Glu$^+$ (left) but not C6Glu$^-$(right) cells. Scale bar, 40 μm. FIG. 5D shows GLT1 immunoreactivity increased around striate implants of C6Glu$^+$ (bottom) but not C6Glu$^-$(top) cells Glioma cells were prelabeled with the cell tracker, CMFDA. GLT1 staining was detected by a Cy3-conjugated antibody. Sections were prepared 4 d after injection of glioma cells. Scale bar, 100 μm. FIG. 5E shows the EAAC1 transporter (Cy3) was expressed in CMFDA-labeled C6Glu$^-$cells (top) but not C6Glu$^+$ cells (bottom) after implant. Scale, 100 μm.

FIG. 6A shows representative tumors in rats with RG2Glu$^+$ (top), RG2Glu$^+$ +memantine (middle) and RG2WT (bottom) cell implants. FIG. 6B shows comparison of RG2 cell tumor size 10 d after implantation of glioma cells. *, P<0.001 (RG2Glu$^+$ versus RG2WT); **, P<0.005 (memantine versus vehicle). FIG. 6C shows proliferation of RG2 glioma cells in presence of 0 (○), 3 (■), 20 (●), 100 (open diamond) or 400 (×) μM memantine. FIG. 6D shows memantine reduced C6Glu$^+$ tumor size 10 d after implantation of glioma cells. *, P<0.001; Student's t-test. FIG. 6E shows proliferation rates of C6Glu$^+$ cells in presence of 0 (○), 3 (■), 20 (●), 100 (open diamond) or 400 (×) μM memantine.

DETAILED DESCRIPTION OF THE INVENTION

Figure 1:
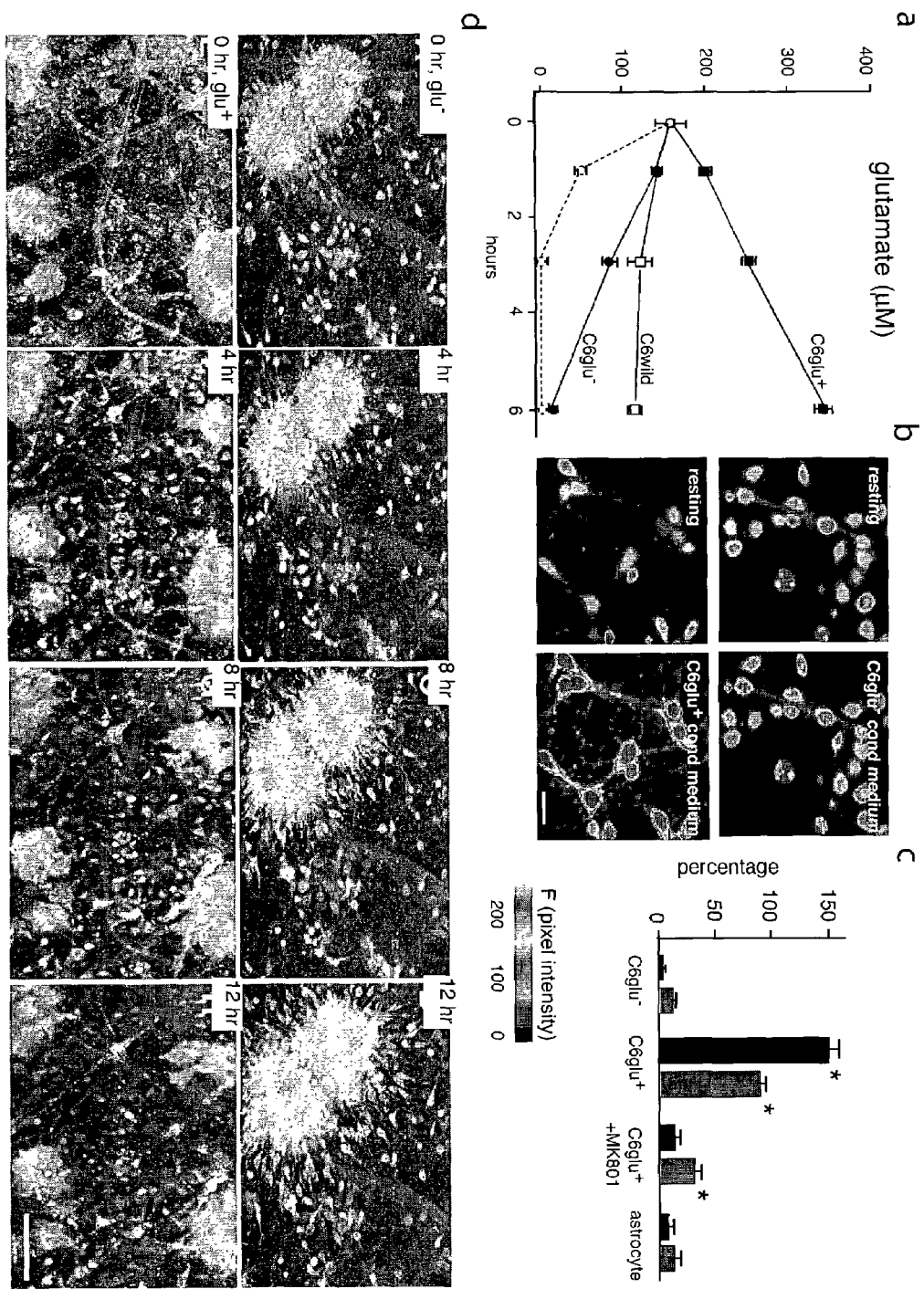
FIGS. 1A–D show glutamate-secreting glioma cells kill co-cultured neurons.

The present invention relates to a method of treating glial tumors in a subject. This method involves providing a glutamate antagonist and administering the glutamate antagonist to a subject with a glial tumor under conditions effective to treat the glial tumor.

Glutamate, the principal excitatory transmitter within the vertebrate nervous system, interacts with two main categories of receptors: ionotropic and metabotropic. Ionotropic glutamate receptors can be subdivided into N-methyl-D-aspartate ("NMDA"), α-amino-3-hydroxy-5-methyl-4-isoxazole-propionate ("AMPA"), and kainate receptors. Each of these types of ionotropic glutamate receptors is made up of subunits. The subunit composition determines the biophysical properties of the receptor and to a variable extent its pharmacology.

Five receptor subunits form the functional NMDA receptor, which is modulated by glycine and polyamines and blocked by Mg$^{2+}$. Activation of NMDA receptors leads to cellular influx of Na$^+$ and K$^+$-ions as well as Ca$^{2+}$-ions, either through the NMDA receptor channel itself or through voltage dependent Ca$^{2+}$-channels (Bettler and Mulle, "Neurotransmitter Receptors II, AMPA and Kainate Receptors," *Neuropharmacology,* 34:123–139 (1995); Mori and Mishina, "Neurotransmitter Receptors VII, Structure and Function of the NMDA Receptor Channel, *Neuropharmacology,* 34:1219–1237 (1995), which are hereby incorporated by reference in their entirety).

Four different subunits, named GluR1, GluR2, GluR3, and GluR4, form the AMPA receptor channel. AMPA receptors are highly permeable to Na$^+$-and K$^+$-ions. AMPA receptor assemblies lacking the GluR2 subunit are also permeable to Ca$^{2+}$-ions (Hollmann and Heinemann, "Cloned Glutamate Receptors, *Annu. Rev. Neurosci.,* 17:31–108 (1994), which is hereby incorporated in its entirety).

Kainate receptors are built from five subunits, GluR5–7 as well as KA1 and KA2. Kainate receptor associated ion channels are permeable to Na$^+$- and K$^+$-ions as well as Ca$^{2+}$. Ca$^{2+}$-permeability of kainate receptor associated ion channels is dependent on the presence of the GluR6 subunit within the receptor complex (Id.).

The interaction of glutamate with its various receptors is implicated in the pathogenesis of neuronal degeneration in the context of hypoxia/ischemia and trauma of the central nervous system, seizures, and hypoglycemia. In addition, glutamate is thought to be involved in the pathogenesis of chronic neurodegenerative disorders, such as amyotrophic lateral sclerosis, Huntington's Disease, Alzheimer's Disease and Parkinson's Disease. Functional glutamate receptors have been identified in lung, muscle, pancreas and bone (Mason et al., *Bone* 20:199–205, 1997; Patton et al., *Bone* 22:645–649 (1998), which are hereby incorporated by reference in their entirety.)

Suitable glutamate antagonists of the present invention include, without limitation, compounds that block glutamate function at ionotropic glutamate receptors. Thus, suitable glutamate antagonists include, for example, compounds that bind ionotropic glutamate receptors. Compounds that bind ionotropic glutamate receptors include compounds which bind AMPA, NMDA, or kainate receptors in a competitive manner or interact with ionotropic glutamate receptor mediated signals in a non-competitive manner.

Suitable glutamate antagonists which bind AMPA receptors include, without limitation, L-glutamate derivatives, amino alkanoic acid derivatives, α-amino-3-hydroxy-5-methyl-4-isoxazolepropionate derivatives, acetyl-aminophenyl-dihydro-methyl-methyl-dioxolobenzodiazepine, acid amide derivatives, amino-phenyl-acetic acid, 2,3-benzodiazepin-4-one, alkoxy-phenyl-benzodiazepine, amino- or desamino 2,3-benzodiazepine, benzothiadiazine, α-carboline-3-carboxylic acid, fused cycloalkylquinoxalinediones, decahydroisoquinoline, 4-hydroxypyrrolone, 4-hydroxypyrrolo-pyridazinone, imidazo-pyrazinone, imidazolo-quinoxalinone, indeno-pyrazine-carboxylic acid, indeno-pyrazinone, indoloneoxime, indolo-pyrazinone, isatine, isatinoxime, oxadiazole, phenyl-azolophthalazine, phenylpyridazino-indole-1,4-dione, quinoline, quinolinone, quinoxaline, quinoxalinedione, quinazolinone, quinolone, nitroquinolone, and sulphamate derivatives.

Suitable glutamate antagonists which bind kainate receptors include, without limitation, L-glutamate derivatives, kainic acid derivatives, acid amide derivatives, aminoalkanoic acid derivatives, aminophenyl(alkyl)acetic acid derivatives, fused cycloalkylquinoxalinediones, quinoxalinedione, imidazolo-quinoxalinone, isatine, phenylazolophthalazine, pyridothiazines, 4-phosphonoalkyl-quinolinone, quinolinone, quinazoline, quinazolinedione, quinoxalinedione, and sulphamate derivatives.

Suitable glutamate antagonists which bind NMDA receptors include, without limitation, L-glutamate derivatives, tetrahydroquinoline, imidazoloquinoxalinone, isatine, fused cycloalkylquinoxalinediones, quinoxaline, spermine, a 4-hydroxy-3-nitro-1,2-dihydroquinolon-2-one derivative, an indole derivative, a benzo-thiadiazine dioxide derivative, an indeno(1,2-b)pyrazin-3-one or corresponding 2,3-dione, a quinoline derivative, an ethyl (phenylcarbamoyl)ethenyl) dichloroindole carboxylate, a thienopyrazine 2,3-dione derivative, a 2-(2,3-dicarboxycyclopropyl) glycine, a 2-amino-3-substituted phenyl propionic acid derivative, 1-carboxyalkylquinoxaline-2,3(1H,4H) dione derivative, a thienyl-glycine derivative, a benzo-fused azacyclic compounds, an indole derivatives, a tricyclic quinoxaline-diene derivative, a 3-hydroxy anthranilic acid and salts, a decahydroisoquinoline compound, a tri- or terta-substituted guanidine derivatives, a D- or L-tryptophan derivative, a tetrazolyl(alkyl)-cyclohexykaminoacid derivative, an octahydrophenanthrene derivative, a benzomorphan compound, a piperazinyl or piperidinyl-alkyl substituted isoxazole derivative, a decahydroisoquinoline-3-carboxylic ester or amide preparation, a compounds based on Conantokin-G peptide, a 3-heterocyclykalkyl-benzopyran-2-one derivative, a phosphono-alkyl imidazo-pyrimidine carboxylic acid derivative, amantidine, memantine, rimantidine, a histogranin peptide or analogue, a nitrobenzoic acid derivative, e.g. 4-((2-methoxycarbonyl-4-nitrophenyl)methyl)piperazine carboxylic acid, a diamine derivative with selective sigma receptor affinity, remacemide (2-amino-N-(1,2-diphenyl-1- methylethyl)acetamide), a phosphono-alkylidene- or phosphono-alkoxyimino-piperidine acid, a benzothiadiazine carboxylic acid derivative, a dihydro-benzothiadiazine dioxide carboxylic acid derivative, a 4-hydroxy 2 (H) pyrrolone derivative, a quinoxaline derivative, a tetrahydro-imidazo (1,2-a) pyrimidines or its salt, a alpha-amino acid, a 4-hydroxy-pyrrolo(1,2-b)pyridazin-2(1H)-one derivative, a nitroquinolone derivative, a 3-aryl-substd 2(1H)quinolone, a 2(1H)-quinolone, a phosphonic acid quinoline-2-carboxylic acid derivative, its per hydro quinoline derivative or salt, a benzimidazole(s) carrying 2 acidic groups, an N,N'-disubstituted guanidine derivative, a tricyclic quinoxaline dione, a 2-(2,3-dicarboxycyclopropyl) glycine stereoisomer, pregnenolone sulphate or one of its derivative, an isatine derivative, a 3-amino-indolyl-derivative, 2-phenyl-1,3-propanediol dicarbamate (felbamate), a benzomorphan derivative, a dihydrothienopyridine derivative, an enantiomer of (aminophenyly heteroaryl ethylamine, a pyridazine-dione derivative, a 2H-1-benzopyran-2-one compound, a 4-sulphonylamino-quinoline derivative, a R(plusy3-amino-1-hydroxy-pyrrolidine-2-one, a 2-carboxy indole, a substd. imino-methano dibenzo (A,D) cycloheptene derivative, an indole-hydrazone, a piperazine derivative, a 4,6-disubstituted tryptophan and kynurenine derivative, a fluorenamine compound, a diketo-pyrido pyrazine derivative or its salts, a 2-amino-3,4-dioxo-1-cyclobutene derivative, a 2-acylamido derivative of 3,4-dihydro-3-oxo-quinoxaline, a benzimidazole phosphono-aminoacid derivative, a quinoxaline phosphono-aminoacid derivative, a piperazine, piperidine or pyrrolidone derivative, ist salts and isomeric forms including stercoisomers, a 4-hydroxy-2(1H)-quinolinone derivative, ist salts and prodrugs, a fused pyrazine derivative, a 2-phenyl or 2-thienyl-(2)-piperidine derivative, a 3-amido or 3-sulphamido-indolyl derivative, a 3-aryl-4-hydroxy-2-(1H)-quinolone derivative, a 2-heterocyclyk2-hydoxy-ethylamine derivative, a 1-aryl-2-aminomethyl pyrrolidine, its optical isomers and acid-addn. salts, a 4,6-dihalo indole2-carboxylic acid derivative, a cyclic aminohydroxamate derivative, a tetracyclic amine derivative, a 2,4-dioxo-1,2, 3,4-tetrahydroquinoline derivative, a 2,4-dioxo-1,2,3,4-tetrahydroquinoline derivative, a 3-phosphonopiperidine and p-pyrrolidine derivative, a benzothieno (2,3-B)-pyrazine-2, 3-(1H,4H)-dione, a spiro dibenzosuberane derivative, a benzomorphan derivative, a preparation of 3,4-disubstituted 2-isoxazoline(s) and isoxazoles(s), a 3-indolyl thio-acetate derivative, an arginine-derived nitric oxide biosynthesis inhibitor, a dicyclic amine derivative, a spiroisoindole derivative, an imidazo(1,2-A)-pyridinylalkyl compound, a 1,2,3,4-tetrahydro-9H-pyrido indole or benzothiophene derivative, an indole-2,3-dione-3-oxime derivative, a 1-aryl-2-(aminomethyl) cyclopropanecarboxamide derivative, a 4-phosphono-2-amino-alkenoic acid derivative, a naphthopyran derivative, a beta-ketone, a beta oxime or beta hydrazine phosphonate, a topa quinone aminoacid, kynurenic acid or a derivative, a quinoline- or thienopyridine-carboxylic acid derivative, a 10,5~(imino-methano)-10,11-dihydro-5H-dibenzo(A,D)cycloheptene or a derivative, a bicyclic aminohydroxamate derivative, an indole-2-carboxylic acid derivative, a substituted adamantane derivative, a benzobicycloalkane derivative, a 2,4-disubstituted-1,2,3,4-tetrahydro-quinoline derivative, a dihydro-alkyl-substituted (immunomethano)-5H-dibenzo-cycloheptene, an aryl cyclohexylamine, an N-substd. benzobicycloalkane amine, an isoquinoline phosphonate derivative, an N,N'-disubstd.-guanidine compound, a phosphonopropenyl piperidine carboxylic acid compound, (2R,3S,4S)-alpha-carboxycyclopropyl-glycine, a pyrrolidine derivative, a dihydroxy-fused heterocyclyl quinoxaline derivative, a hydrogenated derivative of MK801 and analogues, a 5-substd. 10,11-dihydro 5H-dibenzo (A,D) cycloheptene 5,10-imine, an 11-Exo-hydroxy MK 801 preparation including electrochemical cyclisation step to form 5,10-imine bridge in 5-methyl 5-oxyamino 5H-dibenzo (A,D) cycloheptene, a tetra hydro-isoquinoline or 2-benzazepine derivative, an N-3-phenyl-propionyl-substd. spermine or related polyamine derivative, a 4a-amino-fluorene compound or a heterocyclic analogue, a cyclooctane-imine derivative, a R-3-amino-1-hydroxy pyrrolidin-2-one or methionine hydroxamate, a 10,11-dihydro-5H-dibenzo-cyclohepten-5,10-imine compound, a polyhydro-10,11-dihydro-5H-benzo(a,d)cyclohepten-5,10 imine derivative, a 4-oxo-1,4-dihydroquinoline compound with 2-acidic groups, a heterocyclykalkene-phosphonic acid compound, a phosphono gp-containing pyridine 2-carboxylic acid, an alpha-amino-alpha-(3-alkylphenyl)alkyl ethanoic acid, its esters or amides, a 10,11-dihydro-5H-dibenzo-A,D-cyclohepten-5,10-imine compound, a phosphorus containing unsaturated amino acid or its salts, a 5 Substd.-1-, 11-dihydro-5H-dibenzo-cyclohepten-5,10-imine or analogue, a heterocyclic phosphonic acid derivative or its salt, a substituted 4-(aminocarbonyl-amino)quinoline derivative, a tricyclic quinoxaline derivative, a butyryltyrosine spermine or one of its analogue, a tri- or tetra-substituted guanidine, a quinoxalinylalkyl-aminoalkane phosphonic acid derivative, a 2-(aminophenyl)-3-(2-carboxy-indol-3-ylpropenoic acid derivative, a 6-piperidinylpropiony-2 (3H)-benzoxazolone derivative, 6-(3-[4-(4-fluorobenzyl)piperidin-1-yl]propionyly3H-benzoxazol-2-one or one of its salts, an imidazo(1,2-a)pyridine compound, a tetrahydroquinoline derivative or one of its salts, a 2-methyl-5,8-substituted 2,3,4,5-tetra- or 2,3A4a,5,9b-hexahydro-1H-pyrido[4,3-b]indole, a 3-aminoindolyl compound, a 6-pyrrolyl-quinoxaline-2,3-dione derivative, an imidazoly (mercaptoalkyl)-quinoxaline-dione compound, a 3-amidoindolyl derivative, a heterocyclyl-imidazolo-quinoxalinone compound, a naphthyl-substituted alpha-amino acid derivative, a 5-heteroaryl-2,3-quinoxaline-dione derivative, a quinoxaline derivative, a 5H, 1OH-imidazo indeno 4-pyrazinone derivative, a hydroxy-(aryl-substituted phenyl)-quinolone compound, an imidazo indolo pyrazinone derivative, a ((phenyl-amino)-(m) ethylypyridine derivative, a tetrahydro-isoquinoline derivative, a 4-substituted piperidine analogue, a 2-substituted piperidine derivative, a tri- or tetra-substituted guanidine derivative, a 3-Hydroxy-4-imidazolidinone, a 3-aminoquinoxalin-2-one derivative, rapamycin or a derivative e.g. 1,3-Diels Alder adduct with phenyl-triazoline-dione, 1-amino-1-cyclobutanecarboxylic acid, a thiamorphinan derivative, a pyrido[4,3-b]indole derivative, 4-phenyl carbamoyl methylene tetrabydro quinoline-2-carboxylic acid or a derivative thereof, (3R,4SY3-(4-(4-fluorophenyl)-4-hydroxy-piperidin-1-yl)-chroman-4,7-dio a phenol derivative, an indeno-pyrazin-4-one, a 2,3-dioxo-1,2,4,5-tetrahydro-quinoxalinyl derivative, a 45-bridged quinoxalinedione or quinolone, (1S,2S)-1-(4-hydroxyphenyl)2-(4-hydroxy 4-phenyl piperidin-1-yl) I-propanol methane sulphonate trihydrate, a 4-sulphanimide-quinoline derivative, a methanobenzocyclodecen-13-amine compound, a derivatives of pregnenolone sulphate, a quinoxalinyl-(alkane,alkene,or alkyne)-phosphonic acid or one of ist esters, a diarylalkylamine related to spider and wasp venom toxins, a piperazine R-alpha-carboxylic acid derivative, an imidazo-indeno-pyrazin-4-one derivative, a pyridazino-quinoline derivative, a 1-substituted, or 1,3-disubstituted, 1,3-diaryl-guanidine compound, an aza-cycloalkykfused quinoxaline-dione, a 3-substd, 2-carboxy-indole derivative or intermediate, a (2R)-N-trityl-4-oxo-5-(dimethyl phosphono)-nor-valinate ester, a kynurenic acid derivative, an indole carboxylic acid derivative, a 6-(tetrazolyl or isoxazolyl-decahydroisoquinoline-3-carboxylic acid derivative, a phenyl- or pyridinyl-thieno-pyridinone derivative, a fused cycloalkylquinoxaline-dione derivative, a pyridazino-quinoline derivative, a 1-Alpha-amino-3-biphenyi-propanoic acid derivative, a 3-(Indol-3-yl) propenoic acid derivative, a spiro-heterocycle-midazo-indeno-pyrazine-4-one derivative, a 2-heterocyclyk3-indolylpropenoic acid derivative, a piperidinoalkyl heterocyclic ketone or alcohol compound, a pyrrolyl-tetrahydro-benzoquinoxaline-dione derivative, a 7-imidazolyl or dialkylamino,tetrahydroquinoxaline dione compound, a dibenzocycloheptene, a quinoxaline derivative, an aryl-thio-quinoxaline derivative, a heterocyclic substd. imidazolo-quinoxaline derivative, a 1,4-dihydro-quinoxaline-2,3-dione derivative, an oxa- or thia-aliphatically bridged quinoxaline derivative, an aza-aliphatically bridged quinoxaline-2,3-dione compound, a 3-amido- or 3-sulphamido-indole compound, a 3,5-disubstd. phenyl-naphthalene derivative, an imidazo (1,2-a)indeno (1,2-e) pyrazine-2-carboxylic acid derivative, a 3-phenyl-fused ring pyridine-dione derivative, a 2-phenyl-pyridazino-indole-dione derivative, a 4,6-disubstd. kynurenine compound, a phosphono derivative of imidazo(1,2-a) pyrimidine-2-carboxamide, a tetrahydro-quinoxaline-dione derivative with N-(alkyl)carbonyl-amino- or ureido group, a tryptophan derivative, a hetero-aliphatic or hetero-araliphatic substd. quinolone derivative, an imidazo-pyridine dicarboxylic acid derivative, a composition containing pyrazolo-quinoline derivatives, an ethanodihydrobenzo-quinolizinium salt, an oxopyridinylquinoxaline derivative, an indeno-triazolo-pyrazin-4-one derivative, an imidazo-indeno-pyrazinone derivative, an imidazo-indeno-pyrazin-4-one derivative, an imidazo(1,2-a)pyrazine-4-one derivative, a 5H-indeno-pyrazine-2,3-dione derivative, a phenyl-aminoalkyl-cyclopropane N,N-diethyl carboxamide compound, a dexanabinol derivative, a substituted chroman derivative, a sulphonamide quinazoline-2-4-dione compound, a 6-and 8-aza-, and 6,8-diaza-1,4dihydro-quinoxaline-2,3-dione derivative, a substituted quinoline derivative, a tetrazolylalkyl cyclohexyl aminoalkanoic acid, a tricyclic indole 2-carboxylic acid derivative, a 6-substd-7H-imidazo-8-pyrazinone derivative, a quinoxaline dione derivative or one of its radiolabelled compounds, a tricyclic pyridazinopyridine derivative, an N-substituted heterocyclylidenemethyl-indole carboxylic acid derivative, a 3-aza-8-substituted-bicyclo(3.3.0)octane-2-carboxylic acid derivative, an ethano-heterocyclo-isoquinolinium salt, a phenyl alkanolamine derivative, a dihydrobenzothiadiazinedioxide carboxylic acid derivative, a methyl-butenylmethyl(hydroxy-propyl) carbazoledione, an imidazo pyrazinone derivative, an imidazo-(1,2-a)pyrazine-4-one, a benzazepine-dione derivative, disulfiram, a 3-(indol3-yl)-propenoic acid derivative, a 1,2,3,4-tetrahydro-quinoline-2,3,4-trione-3 or 4-oxime compound, a peptide antagonist at NMDA receptors, a 2-amino-2phenyl(alkylyacetic acid derivative, 6-halo-tryptophan or a 4-halo-kynurenine, a 6-tetrazolyl or isoxazoly-decahydro-isoquinoline-3-carboxylic acid derivative, or an imidazolyl-benzene or salts thereof Suitable glutamate antagonists of the present invention also include compounds that interact with ionotropic glutamate receptor ion channels. Thus, compounds that interact with AMPA, NMDA, and kainate receptor ion channels are suitable glutamate antagonists of the present invention. These compounds reduce the permeability of channels associated with ionotropic receptor cations.

Glutamate antagonists that interact with AMPA receptor ion channels refer to compounds that reduce the permeability of channels associated with the AMPA receptor cations (preferably to $Na^+$, $K^+$ and/or $Ca^{2+}$ ions). Glutamate antagonists that interact with AMPA receptor ion channels can therefore be used to prevent a signal being transmitted due to ionic flux that would otherwise occur when glutamate binds to the AMPA receptor. Suitable compounds include, without limitation, fluorowillardiine, Joro spider toxin, NSTX spider toxin, and argiotoxin.

Glutamate antagonists that interact with kainate receptor ion channels refer to compounds that reduce the permeability of channels associated with the kainate receptor cations (preferably to $Na^+$, $K^+$ and/or $Ca^{2+}$ ions). Glutamate antagonists interacting with kainate receptor ion channels can therefore be used to prevent a signal being transmitted due to ionic flux that would otherwise occur when glutamate binds to the kainate receptor. Suitable compounds include, without limitation, Joro spider toxin, NSTX spider toxin, and argiotoxin 636.

Glutamate antagonists that interact with NMDA receptor ion channels refer to compounds that prevent the influx of $Na^+$, $K^+$, or $Ca^{2+}$ ions into the cell. Glutamate antagonists interacting with NMDA receptor ion channels can therefore be used to prevent a signal being transmitted due to ionic flux that would otherwise occur when glutamate binds to the NMDA receptor. Suitable compounds include, without limitation, magnesium, dizocilpine, phencyclidine, ketamine, memantine, tiletamine, budipine, flupirtine, 1-[1-(2-thienyl) cyclohexyl]piperidine (TCP), and (+)-(3S,4S)-7-hydroxy-delta6-tetrahydrocannabinol-1,1-dimethylheptyl (HU211).

Agents or compounds that decrease the release of glutamate are also deemed suitable glutamate antagonists of the present invention, as are agents that decrease the synthesis of glutamate. Such agents include, without limitation, riluzole, lamotrigine, diphenylhydantoin, tetrodotoxin, aga-toxin-glutamate-release-inhibitor (AG-GI), [5-(2,3,5-trichlorophenyl)]-2,4-diamino-pyrimidine (BW1003C87), (R)-(-)-5-methyl-1-nicotinoyl-2-pyrazoline (MS-153) and 4-amino-2-(4-methyl-1-piperazinyl)-5-(2,3,5-trichlorophenyl) pyrimidine (BW619C89).

Agents that increase the metabolism or uptake of glutamate, and thereby block the activity of glutamate at ionotropic glutamate receptors, are also suitable glutamate antagonists for the methods of the present invention.

Suitable glutamate antagonists may also increase glutamate uptake. For example, these compounds decrease synaptic concentration of glutamate by activating uptake mechanisms for glutamate preventing activation of either AMPA, kainate or NMDA receptors. Compounds accelerating glutamate uptake mechanisms include e.g., 5-glutamyl-transpeptidase.

Agents that interact directly with glutamate are also suitable glutamate antagonists of the present invention. Such agents would include compounds classified as glutamate partial agonists or molecules binding glutamate directly. In addition, antibodies to ionotropic receptor subunits, ionotropic receptors, or glutamate itself, are suitable glutamate antagonists of the present invention. Accordingly, the suitable antibodies function to decrease or prevent the binding of glutamate to ionotropic binding sites, thus preventing glutamate from triggering the signal that would occur as a result of the binding of glutamate to ionotropic binding sites.

Agents that interact with glutamate and prevent its binding to ionotropic receptors are also suitable glutamate antagonists. Such agents include partial agonists and molecules binding to glutamate which change the conformational state of glutamate and therefore decrease its binding capability to its receptors. Glutamate partial agonists activate ionotropic glutamate receptors by themselves but are less active than glutamate at these receptors and, therefore, decrease activation of these receptors by glutamate at physiological and excessively high concentrations, and include, without limitation, D-serine, D-cycloserine, 5-L-glutamylglutamate, N-phthalamoyl-L-glutaminic acid, (R,S)-2-amino-3-[5-tert-butyl-3(phosphonomethoxy)-4-isoxazolyl] propionic acid, $\alpha$-N-acetylaspartylglutamate, 1-aminocyclopropanecarboxylic acid, aminocyclobutane cyrboxylic acid, (+,R(3-amino-1-hydroxy-2-pyrrolidine (HA966) and D,L-threo-3-hydroxyasparate. Furthermore, such agents include soluble forms of NMIDA, kainate, or AMPA receptors or parts thereof. These soluble forms can be used to circulate and to bind to glutamate and therefore decrease its binding capability to the receptors. Membrane bound forms of the glutamate receptors may also be incorporated into liposomes, to circulate and bind to glutamate so as to prevent its binding to ionotropic receptors.

The AMPA, kainate or NMDA receptors or a part or parts of them, or glutamate can be used for raising antibodies that bind thereto. Antibodies that bind to AMPA, kainate, or NMDA receptors, or parts of them, are suitable glutamate antagonists of the present invention. Preferred antibodies bind specifically to either AMPA, kainate, or NMDA receptor or a part thereof, or to glutamate. The antibodies may be monoclonal or polyclonal. Polyclonal antibodies can be raised by stimulating their production in a suitable animal host (e.g. a mouse, rat, guinea pig, rabbit, sheep, goat or monkey) when either AMPA, kainate, or NMDA receptor, or a part thereof, or glutamate is injected into the animal. If necessary an adjuvant may be administered together with the AMPA, kainate, or NMDA receptor, or a part thereof, or with glutamate. In addition to whole antibodies, antagonists of the present invention include derivatives thereof.

In accordance with the present invention, the glutamate antagonist is administered under conditions effective to treat the glial tumor. As used herein, treating the glial tumor encompasses either reducing the growth of glial tumors in the living system, reducing the symptomatic events associated with glial tumor growth in the living system, or both. Treatments may be prophylactic or may be in respect of existing conditions.

Effective amounts of the glutamate antagonist will depend upon the mode of administration, frequency of administration, nature of the treatment, age and condition of the individual to be treated, and the type of pharmaceutical composition used to deliver the compound into a living system. Effective intracerebral levels of glutamate antagonists may range from 50 nM to 5 $\mu$M (given to experimental animals as 20–30 mg/kg twice daily for ten days), depending upon the compound, system, experimental and clinical endpoints, and toxicity thresholds. For example, the glutamate antagonist memantine may be used for this purpose with great efficacy at 25 mg/kg twice daily (Takano et al., Nature Med. 7:1010–15 (2001), which is hereby incorporated by reference in its entirety). While individual doses vary, optimal ranges of effective amounts may be determined by one of ordinary skill in the art. For glutamate antagonists that are involved in clinical trials for other indications, the safe and effective dosages identified in such trials can be considered when selecting dosages for treatments according to the present invention.

The glutamate antagonists used according to the methods of the present invention can be administered alone or as a pharmaceutical composition, which includes the compound(s) and a pharmaceutically-acceptable carrier. The glutamate antagonists are typically provided as a pharmaceutical composition. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent of active compound(s), together with the carrier.

The glutamate antagonist, when combined with pharmaceutically or physiologically acceptable carriers, excipients, or stabilizers, whether in solid or liquid form such as, tablets, capsules, powders, solutions, suspensions, or emulsions, can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes, such as, that of the nose, throat, and bronchial tubes (i.e., inhalation).

For most therapeutic purposes, the glutamate antagonists can be administered orally as a solid or as a solution or suspension in liquid form, via injection as a solution or suspension in liquid form, or via inhalation of a nebulized solution or suspension. The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose, and related sugar solution, and glycols, such as propylene glycol or polyethylene glycol, are preferred liquid carriers, particularly for injectable solutions.

For use as aerosols, the compound in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

For transdermal routes, the compound is present in a carrier which forms a composition in the form of a cream, lotion, solution, and/or emulsion. The composition can be included in a transdermal patch of the matrix or reservoir type as are conventional in the art for this purpose.

It is also contemplated that administration of the glutamate antagonist can be carried out in combination with other suitable therapeutic treatments which are useful for treating glial tumors.

A second aspect of the present invention relates to a method of treating glial tumors in a living system, which includes providing a NMDA receptor antagonist and administering the NMDA receptor antagonist to a living system with a glial tumor under conditions effective to treat the glial tumor.

EXAMPLES

The following examples are provided to illustrate embodiments of the present invention but are by no means intended to limit its scope.

Example 1

Primary Cultures and Cell Lines

Cortical neurons were prepared from Wistar rats (16 days gestation; Taconic, Germantown, N.Y.) and plated in 24-well plates (Nedergaard, M., "Direct Signaling From Astrocytes to Neurons in Cultures of Mammalian Brain Cells," *Science*, 263:1768–1771 (1994), which is hereby incorporated in its entirety). Cortical astrocytes were prepared from 1-day postnatal rate pups (Cotrina et al., "Astrocytic Gap Junctions Remain Open During Ischemic Conditions," *J. Neurosci.*, 18:2520–2537 (1998), which is hereby incorporated in its entirety), whereas C6 and RG2 glioma cells were obtained from American Type Culture Collection (Lin et al., "Ga-Junction-Mediated Propagation and Amplification of Cell Injury," *Nature Neurosci.*, 1:494–500 (1998), which is hereby incorporated in its entirety) (Manassas, Va.). All cultures were grown in DMEM/F12 supplemented with 10% FBS, 20 mM glucose and antibiotics.

Example 2

Cocultures of Neurons and Glioma Aggregates

Glioma cell aggregates were produced by plating 100,000 C6Glu$^+$ or C6Glu$^-$ cells in plates with non-adhesive substrate (ultra low cluster 3473; Costar, Cambridge, Mass.). Twenty-four hours later, the glioma aggregates were loaded with calcein AM (green, 2 µM, excitation 488 nm) and transferred to neuronal cultures. Cortical neuronal cultures were preloaded with the cell tracker Sytox 62 (white, 0.1 µM, excitation 647 nm). Loss of neuronal viability was quantified as the percentage of neurons that displayed nuclear staining with propidium iodide (red, 1 µM, excitation 567 nm) at 12 or 24 hours after coculturing (Cotrina et al., "Astrocytic Gap Junctions Remain Open During Ischemic Conditions," *J. Neurosci.*, 18:2520–2537 (1998); Nedergaard, M., "Direct Signaling From Astrocytes to Neurons in Cultures of Mammalian Brain Cells," *Science*, 263:1768–1771 (1994), which are hereby incorporated in its entirety).

Example 3

Calcium Measurements, Cell Proliferation, and Migration Assays

Ten-day-old cortical neurons were loaded with the calcium indicator, fluo-3 AM (5 µM, 1 h), and the fluorescence signal was detected by confocal microscopy (MRC1000, BioRad, Richmond, Calif.) as described (Lin et al., "Ga-Junction-Mediated Propagation and Amplification of Cell Injury," *Nature Neurosci.*, 1:494–500 (1998); Zhang et al., "Tamoxifen-Induced Enhancement of Calcium Signaling in Glioma and MCF-7 Breast Cancer Cells," *Cancer Res.*, 60:5395–5400 (2000), which are hereby incorporated in their entirety). 100 µl conditioned medium from the C6 clones was added to the culture (initial media volume was 300 µl). Proliferation of the C6 subclones was determined by cell counting or by the Alamar blue assay (Biosource, Camarillo, Calif.) and cellular invasiveness evaluated using Matrigel-coated transwell inserts as described (Zhang et al., "Direct Gap Junction Communication Between Malignant Glioma Cells and Astrocytes," *Cancer Res.*, 59:1994–2003 (1999), which is hereby incorporated in its entirety).

Example 4

Glutamate Measurements

Confluent cultures were washed twice and incubated in fresh culture medium. Samples of the supernatant were collected at 1, 3 and 6 hours. Glutamate concentration was quantified using a bioluminescence assay (Fosse et al., "A Bioluminescence Method for the Measurement of L-Glutamate: Applications to the Study of Changes in the Release of L-Glutamate from Lateral Geniculate Nucleus and Superior Colliculus After Visual Cortex Ablation in Rats," *J. Neurochem.*, 47:340–349 (1986); Innocenti et al., "Imaging Extracellular Waves of Glutamate During Calcium Signaling in Cultured Astrocytes," *J. Neurosci.*, 20:1800–1808 (2000), which are hereby incorporated in their entirety) and luminescence read by a plate reader (Victor2, Perkin-Elmer, Norwalk, Conn.). Glutamate release from freshly prepared brain slices was imaged by preparing 300-µm slices by vibratome 5 days after tumor implantation. The sections were prepared in artificial CSF as described (Kang et al., "Astrocyte-Mediated Potentiation of Inhibitory Synaptic Transmission,"*Nature Neurosci.*, 1:683–692 (1998), which is hereby incorporated in its entirety). After 15 to 30 min. incubation in CSF, the slices were transferred to microscope stage and immersed in the bioluminescence mixture (1 ml) at room temperature. To modify the bioluminescence mixture to be tolerated by live tissue, glycerol was removed using Hank's buffered salt solution as the base. The luminescence was imaged by an intensified CCD camera (Hamamatsu, C2400) attached to a BX-50 microscope with a 50 mm camera lens (Olympus). The relative light production over the tumor versus normal brain tissue was quantified. Light emission higher than a background threshold was superimposed upon a bright-field image of the same section obtained immediately after luminescence recordings. The brain slices were fixed overnight in 4% paraformaldehyde and stained with cresylviolet.

Glutamate uptake was analyzed by mixing 0.4 µCi/ml L-[$^3$H]glutamate (specific activity 0.03 Ci/mmol) with 150 µM glutamate in a buffer containing 140 nM NaCl, 1.5 mM $K_2HPO_4$, 2 MM $MgCl_2$, 2 mM $CaCl_2$, 10 mM HEPES and 10 mM glucose with pH 7.3 (ref 6). NaCl was replaced by choline chloride for sodium-free conditions. Cells were washed twice, then incubated in the uptake solution with various blockers for 5 min., followed by 3 washes with ice-cold buffer, and then dissolved in 0.3 N NaOH. The activity of [$^3$H]glutamate was detected with liquid scintillation counter (1209 Rackbeta, LKB Wallac, San Francisco, Calif.). Protein concentration was determined by using the DC protein assay kit from BioRad.

Example 5

Glioma Implantation

Rats (male Wistar, 250–270 g) anesthetized with pentobarbital (50 mg/kg) were placed in a stereotactic frame and 1×10⁴ C6 cells were injected at a depth of 6 mm in the right striata with a Hamilton syringe. Injection coordinates with regard to bregma were 0.5 mm posterior and 3.0 mm lateral. Fischer rats (170–200 g) were injected with 1×10⁴ RG2 cells. In some experiments, the glioma cells were prelabeled with the cell tracker, CMFDA (2 μM, Molecular Probes, Eugene, Oreg.) (Lin et al., "Ga-Junction-Mediated Propagation and Amplification of Cell Injury," *Nature Neurosci.*, 1:494–500 (1998), which is hereby incorporated in its entirety). Ten days after implantation, the anesthetized rats were perfused with 4% paraformaldehyde in phosphate buffer. After post-fixation for 24 hours, the brains were sectioned into 50–500-μm slices by a vibratome (Kang et al., "AstrocyteMediated Potentiation of Inhibitory Synaptic Transmission," *Nature Neurosci.*, 1:682–692 (1998), which is hereby incorporated in its entirety). The slices were imaged using a Sony digital camera (DSC-S50) and tumor volume calculated using NIH Image software.

Example 6

Immunohistochemistry

Polyclonal antibodies against glutamate transporters were supplied by and used as described by Rothstein et al., "Localization of Neuronal and Glial Glutamate Transporters," *Neuron*, 13:713–725 (1994), which is hereby incorporated in its entirety. Neuronal death was visualized with the TUNEL technique (Oncor, Gaithersburg), and counterstained with hematoxilin and eosin (H&E) (Lin et al., "Ga-Junction-Mediated Propagation and Amplification of Cell Injury," *Nature Neurosci.*, 1, 494–500 (1998), which is hereby incorporated in its entirety). Double labeling for TUNEL and MAP-2 (clone HM-2, Sigma) or GFAP (G3893, Sigma) was performed as described (Nedergaard, M., "Direct Signaling From Astrocytes to Neurons in Cultures of Mammalian Brain Cells," *Science*, 263:1768–1771 (1994), which is hereby incorporated in its entirety). TUNEL⁺ neurons within a distance of 200 μm from the tumor border were counted by a blinded observer. Microglia were visualized with a monoclonal antibody (ED-1, MCA341R, Serotec, Raleigh, N.C.).

Example 7

Glioma Glutamate Release Triggers Neuronal Death in Vitro

To investigate whether glutamate excitotoxicity contributes to tumor expansion, glioma cell lines, differing by their potential to secrete glutamate, were subcloned. The C6 glioma cell line endogenously expresses the excitatory amino acid carrier 1 (EAAC1) and is characterized by a slow uptake of glutamate (Palos et al., "Rat C6 and Human Astrocytic Tumor Cells Express a Neuronal Type of Glutamate Transporter," *Brain Res. Mol. Brain Res.*, 37:297–303 (1996); David et al., "Multiple Signaling Pathways Regulate Cell Surface Expression and Activity of the Excitatory Amino Acid Carrier 1 Subtype of Glu Transporter in C6 Glioma," *J. Neurosci.*, 18:2475–2485 (1998), which are hereby incorporated in their entirety). (FIG. 1A). Subcloning of C6 cells produced several clones that either actively released glutamate (C6Glu⁺ cells) or showed enhanced uptake of glutamate (C6Glu⁻ cells). These subclones were selected after repeated quantification of glutamate uptake/release with 18 subclones over a 4-month period. The 18 subclones grouped as follows: 5 subclones showed glutamate uptake, 6 subclones neither took up nor released glutamate, such as wild-type C6 (C6WT), whereas 4 subclones released moderate and 3 subclones high levels of glutamate.

After transfer of conditioned medium from C6Glu⁺ cells to cultured cortical neurons that had been first loaded with the calcium indicator fluo-3, there was a rapid increase in the relative emission of fluo-3, indicating increased cytosolic calcium levels (FIG. 1B). The increase in fluo-3 emission was blocked by the noncompetitive NMDA receptor antagonist, MK801 (10 μM; Cotrina et al., "Astrocytic Gap Junctions Remain Open During Ischemic Conditions," *J. Neurosci.*, 18:2520–2537 (1998); Nedergaard, M., "Direct Signaling From Astrocytes to Neurons in Cultures of Mammalian Brain Cells," *Science*, 263:1768–1771 (1994), which are hereby incorporated in their entirety) (FIG. 1C). In contrast, conditioned medium obtained from C6Glu⁻ cells evoked only marginal changes in the fluo-3 signal (FIG. 1B).

To study the direct cellular interactions, the glioma clones were cocultured with cortical neurons (Id.). Twenty-four hours after adding aggregates of C6Glu⁻ cells to established neuronal cultures, 86±2% of the neurons remained viable (FIGS. 1C–D). In comparison, only 14±1% of neurons survived in sister cultures after addition of C6Glu⁺ cell aggregates (FIGS. 1C–D). Glutamate excitotoxicity mediated much of the injury, as pretreatment with MK801 attenuated the neuronal loss (FIG. 1C). These results indicate that glioma cells can release neurotoxic concentrations of glutamate in vitro.

Example 8

Loss of EAAC1 in Glutamate Releasing Glioma Cells

Figure 2:
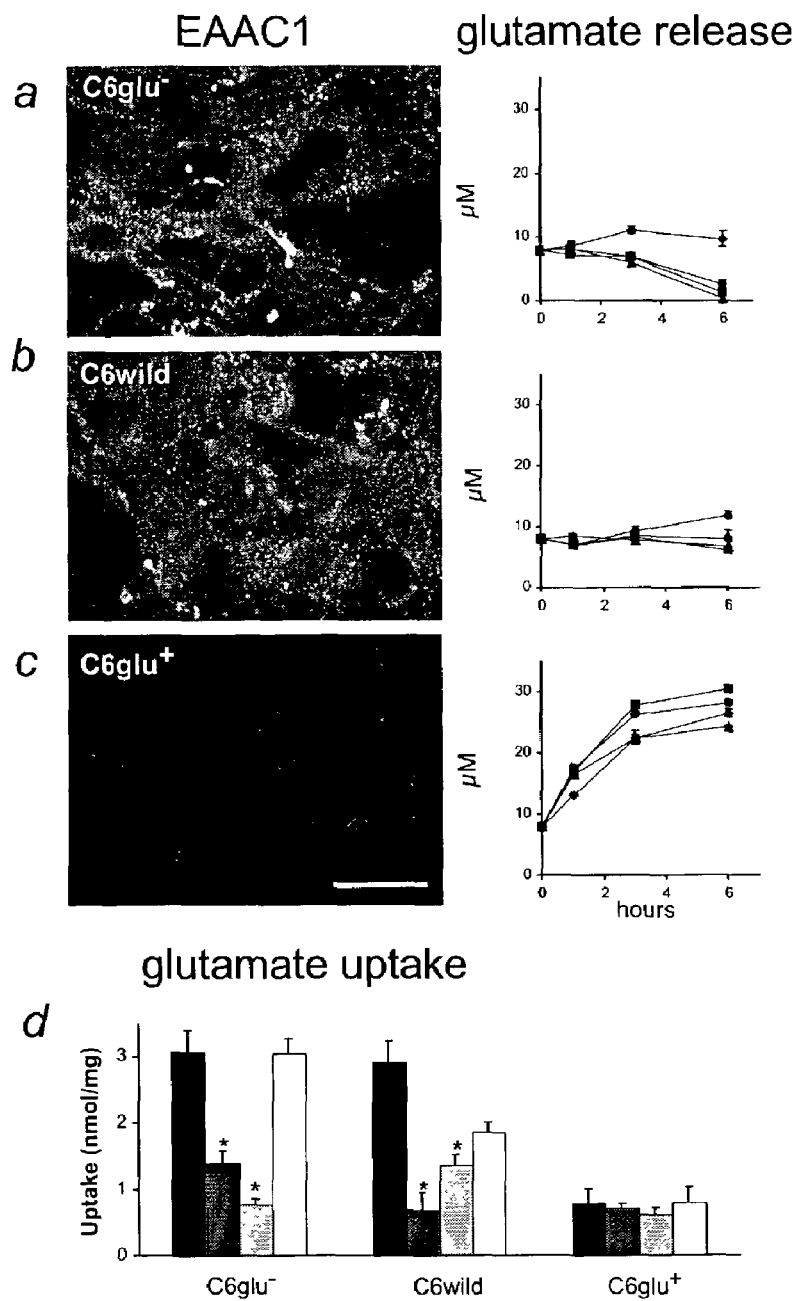
FIGS. 2A–D show expression and properties of glutamate transporter in C6 subclones.

It was next tested whether glutamate secretion from gliomas was a result of reversal of glutamate transport. Immunocytochemical analysis showed that C6WT expressed the EAAC1 transporter, but not glutamate-aspartate transporter (GLAST) or glutamate transporter-1 (GLT1), in agreement with earlier reports (Palos et al., "Rat C6 and Human Astrocytic Tumor Cells Express a Neuronal Type of Glutamate Transporter," *Brain Res. Mol. Brain Res.*, 37:297–303 (1996); Rothstein et al., "Localization of Neuronal and Glial Glutamate Transporters," *Neuron*, 13:713–725 (1994) which are hereby incorporated in their entirety). (FIG. 2A–C). EAAC1 expression was lost in C6Glu⁺ cells (FIG. 2C), but not in the C6Glu⁻ cell line (FIG. 2A), indicating that lack of glutamate uptake contributed to the accumulation of extracellular glutamate in C6Glu⁺ cell cultures. Functional assays confirmed the lack of EAAC1 expression in C6Glu⁺ cells, because uptake of [³H] glutamate in C6Glu⁺ cells was not affected by removal of extracellular sodium and the transport inhibitor trans-pyrrolidine-2,4-dicarboxylate (trans-PDC; 200 μM). In contrast, [³H]glutamate uptake in C6Glu⁻ and C6WT cells, both of which express EACC1, was significantly reduced by removal of sodium or addition of trans-PDC (FIG. 2D). However, the data do not indicate that glutamate release from C6 cells resulted from reversal of glutamate transport, as glutamate release was not affected by trans-PDC and because EEAC1 expression was lost in C6Glu⁺ cells (FIGS. 2A–C). Moreover, reversal of glutamate transport does not contribute to glutamate release from cultured brain slices (Jabaudon et al., "Inhibition of Uptake Unmasks Rapid Extracellular Turnover of Glutamate of Nonvesicular Origin," *Proc. Natl. Acad. Sci. USA*, 96:8733–8738 (1999), which is hereby incorporated in its entirety). The cystine-glutamate exchanger system did not mediate glutamate release from C6 cells either, because addition of extracellular cystine or an inhibitor of the exchanger (s)-4-carboxyphenylglycine (S-4CPG; 100 µM) had no effect upon glutamate release from any of the three cell types of clones studied (Warr et al., "Modulation of Extracellular Glutamate Concentration in Rat Brain Slices by Cystine-Glutamate Exchange," *J. Physiol.*, 514:783–793 (1999), which is hereby incorporated in its entirety).

Example 9

Glutamate-secreting Glioma Implants Show Growth Advantage

Figure 3:
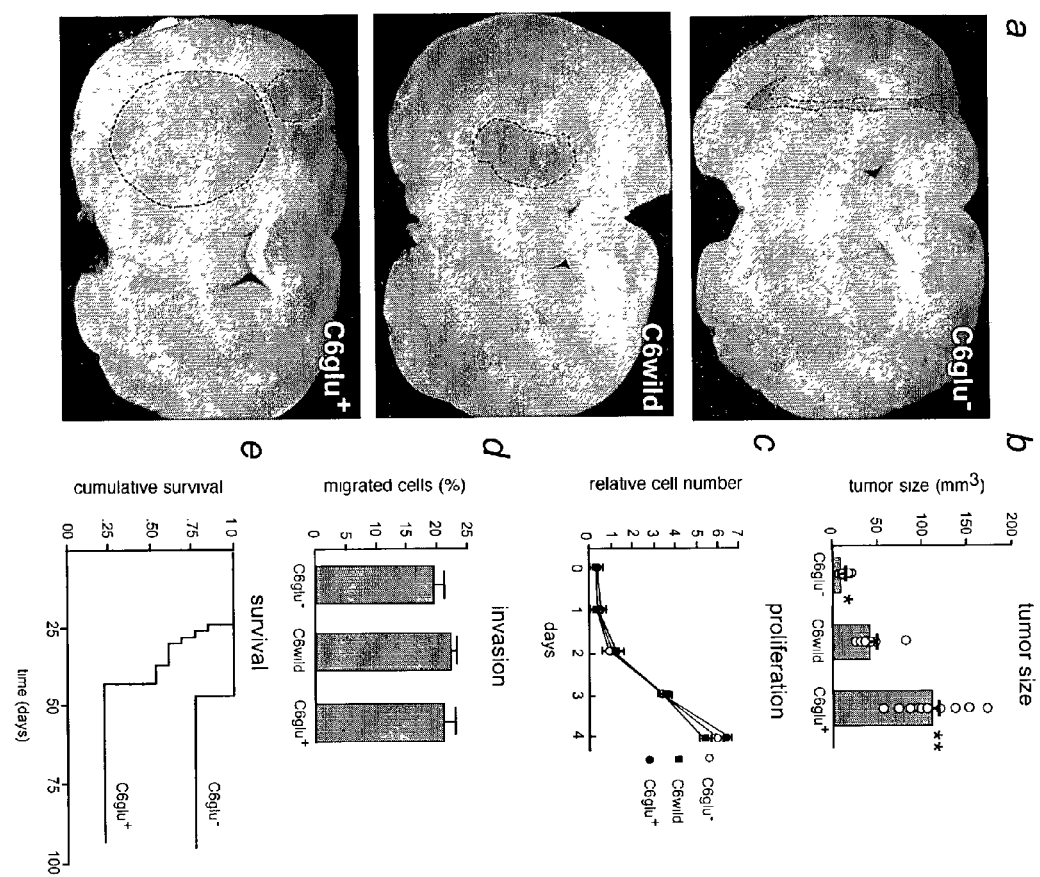
FIGS. 3A–E shows glutamate-secreting gliomas expand rapidly.

To evaluate the effect of glioma glutamate release in brain, the cell clones were implanted in striata of adult rats (Zhang et al., "Direct Gap Junction Communication Between Malignant Glioma Cells and Astrocytes," *Cancer Res.*, 59:1994–2003 (1999), which is hereby incorporated in its entirety). Tumor size was assessed 10 days after implantation. Rats injected with C6Glu$^+$ cells developed aggressive tumors that expanded three-fold faster than tumors composed of C6WT cells (FIGS. 3A–B). In contrast, rats that received C6Glu$^-$ cell implants had uniformly small tumors. Ten days after implantation, most of the C6Glu$^-$ cells failed to establish tumors beyond the limits of the injection track (FIG. 3A). The difference in tumor size did not reflect intrinsic difference in their mitotic rate, as the proliferation of C6Glu$^-$ and C6Glu$^+$ cells did not differ significantly from C6WT cells (FIG. 3C). C6WT, C6Glu$^+$ and C6Glu$^-$ cells also displayed similar degrees of invasiveness through matrigel in trans-well chambers. When assessed at 48 hours, roughly one third of the cell population had transited to the lower side of the test membrane, irrespective of their capacity to release glutamate (Zhang et al., "Direct Gap Junction Communication Between Malignant Glioma Cells and Astrocytes," *Cancer Res.*, 59:1994–2003 (1999), which is hereby incorporated in its entirety). (FIG. 3D).

Survival studies supported the notion that glutamate-secreting gliomas expanded faster. Rats injected with C6Glu$^-$ survived significantly longer than rats with C6Glu$^+$ implants: 10 of 13 rats (77%) injected with C6Glu$^-$ cells, compared with 3 of 13 rats (23%) with C6Glu$^+$ implants, were alive at day 90 (FIG. 3E, P<0.002). Together, the results indicate that glutamate secretion confers implanted glioma cells with a distinct growth advantage in vivo which is not apparent under in vitro culture conditions.

Example 10

The NMDA Antagonist MK801 Slows Tumor Expansion

Figure 4:
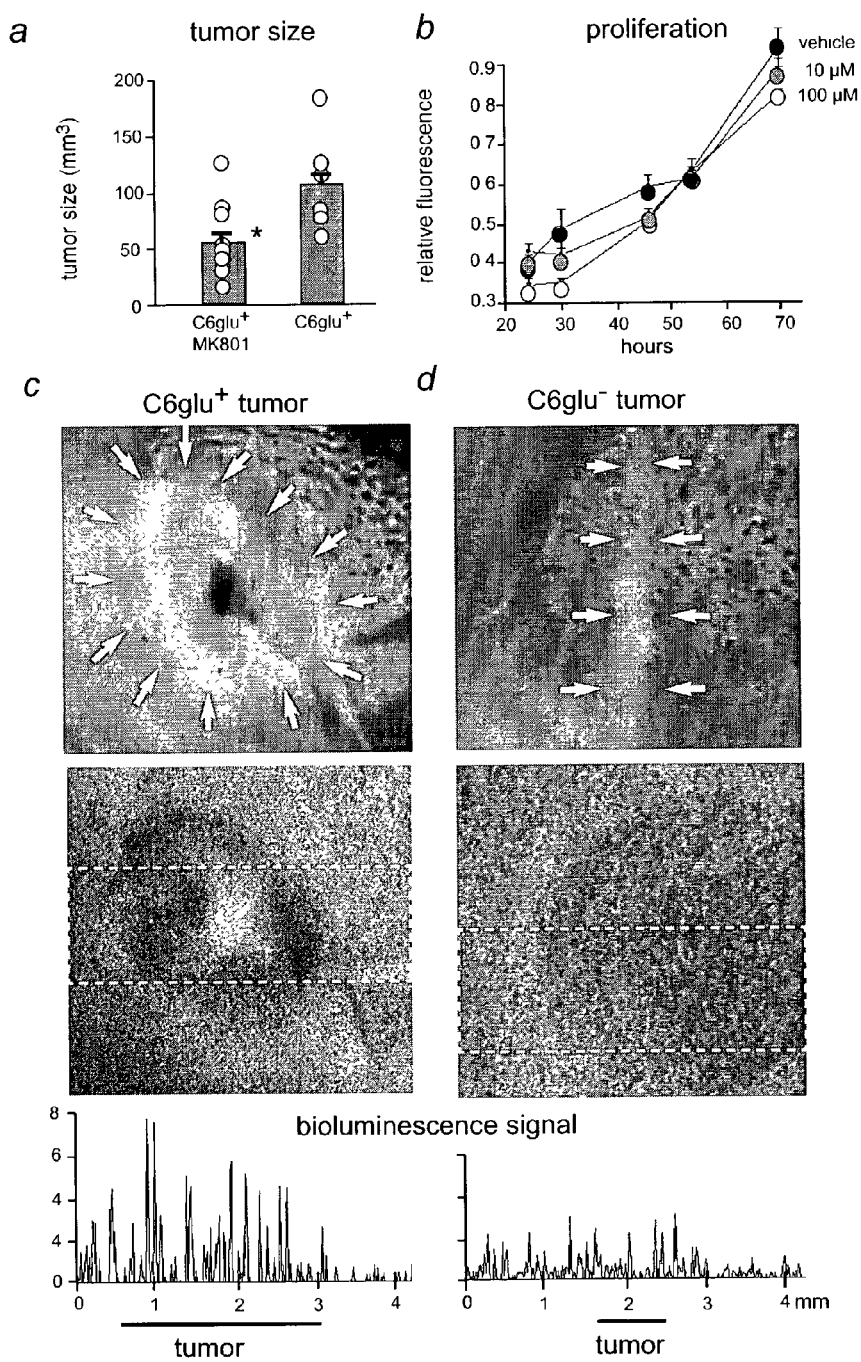
FIGS. 4A–D show MK801 reduces expansion of glutamate-secreting gliomas.

Based upon the above observations, it was investigated whether excitotoxic neuronal death accelerates tumor expansion. The results show that administration of the NMDA receptor antagonist MK801 (dizocilpine, 1 mg/kg twice daily, intraperitoneally (i.p.)) significantly attenuated the growth of C6Glu$^+$ cell implants. Tumors averaged 54.9±11 mm$^3$ in MK801-treated animals compared with 106±19 mm$^3$ in vehicle-treated control animals 10 days after injection (P<0.001, one-way ANOVA) (FIG. 4A). MK801 did not reduce the proliferation rate of C6 cells in vitro (FIG. 4B).

Example 11

Bioluminescence Detection of Glutamate Release in Vivo.

To test whether glioma cells implanted into host brain continued to secrete significant amounts of glutamate, a system was developed, in which glutamate release from freshly prepared brain slices could be imaged using bioluminescence. The bioluminescence assay detects glutamate by combining glutamate dehydrogenase-catalyzed NADH production with the luciferase reaction. The photons of light produced by the reaction were collected by an intensified CCD camera (Fosse et al., "A Bioluminescence Method for the Measurement of L-Glutamate: Applications to the Study of Changes in the Release of L-Glutamate from Lateral Geniculate Nucleus and Superior Colliculus After Visual Cortex Ablation in Rats," *J. Neurochem.*, 47:340–349 (1986); Innocenti et al., "Imaging Extracellular Waves of Glutamate During Calcium Signaling in Cultured Astrocytes," *J. Neurosci.*, 20:1800–1808 (2000), which are hereby incorporated in their entirety). It was found that the photon emission from the C6Glu$^+$ tumors was two-fold higher than from the surrounding host brain, whereas the photon emission from C6Glu$^-$ tumors was not (FIGS. 4C–D). Thus, C6Glu$^+$ cells continue to secrete glutamate after implantation resulting in a detectable elevation of extracellular glutamate, as previously noted using microdialysis (Behrens et al., "Extracellular Glutamate and Other Metabolites in and Around RG2 Rat Glioma: An Intracerebral Microdialysis Study," *J. Neurooncol.*, 47:11–22 (2000), which is hereby incorporated in its entirety).

Example 12

Neuronal Degeneration in Tumor Vicinity

Figure 5:
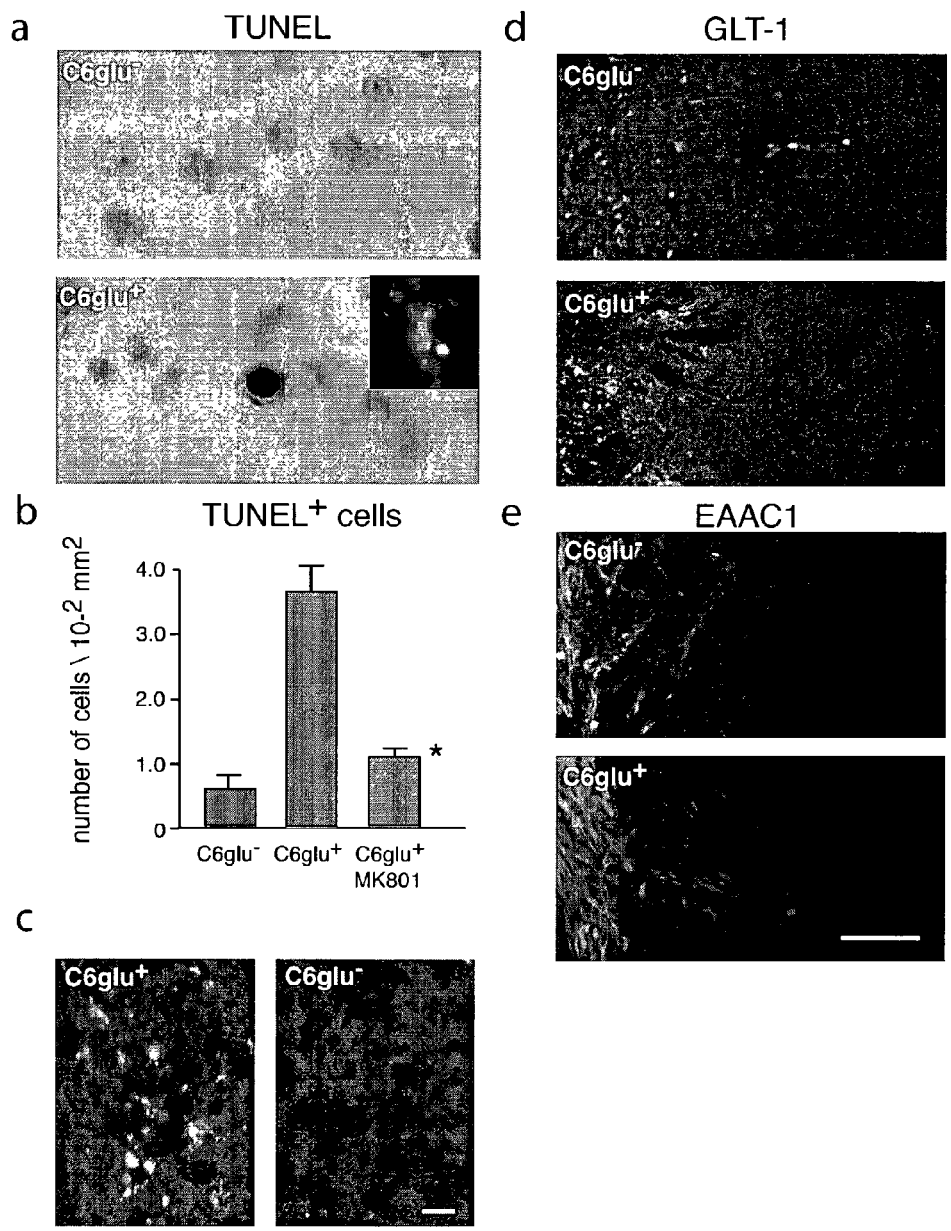
FIGS. 5A–E show neuronal death and inflammatory response surrounding glutamate-secreting tumors.

To test the possibility that elevation of extracellular glutamate triggers excitotoxic neuronal death in normal brain tissue invaded by C6Glu$^+$ tumor cells, TUNEL (terminal deoxynucleotidyl-transferase-mediated dUTP-biotin nick end-labeling) staining was used to identify degenerating neurons (Lin et al., "Ga-Junction-Mediated Propagation and Amplification of Cell Injury," *Nature Neurosci.*, 1, 494–500 (1998), which is hereby incorporated in its entirety). Five-day-old tumors were evaluated to minimize indirect injury resulting from the very large tumors in animals with C6Glu$^+$ cell implants. Consistent with the coculture experiments (FIG. 1D), a marked number of degenerated neurons positive for the microtubule-associated protein-2 (MAP-2$^+$) surrounded C6Glu$^+$ tumor implants. (FIG. 5A). The density of TUNEL$^+$ neurons in the tissue surrounding implanted C6Glu$^+$ cells varied from 2 to 12 per $1\times10^{-2}$ mm$^2$ whereas the density was 0 to 2 per $1\times10^{-2}$ mm$^2$ near C6Glu$^-$cell tumors (FIG. 5B). As administration of MK801 reduced the number of TUNEL$^+$ neurons surrounding C6Glu$^+$ cell tumors (FIG. 5C, P<0.001 by one-way ANOVA), neuronal death was mediated by NMDA receptor activation. TUNEL$^+$ cells were not positive for glial fibrillary acidic protein (GFAP), indicating the GFAP$^+$ astrocytes did not degenerate in tumor surroundings. Rather, it was observed that reactive hypertrophic astrocytes intensely labeled against GFAP in tumor surroundings. Numerous ED1$^+$ microglia cells surrounded C6Glu$^+$ cell tumors, but were essentially absent around C6Glu$^-$tumors (FIG. 5C). The inflammatory response in tissue surrounding C6Glu$^+$ tumors might be a result of excitotoxic neuronal death (Scali et al., "Brain Inflammatory Reaction in an Animal Model of Neuronal Degeneration and its Modulation by an Anti-Inflammatory Drug: Implication in Alzheimer's Disease," *Eur. J. Neurosci.*, 12: 1900–1912 (2000), which is hereby incorporated in its entirety), but a direct inflammatory effect of glutamate cannot be excluded (Bolton et al., "Differential Blood-Brain Barrier Breakdown and Leucocyte Recruitment Following Excitotoxic Lesions in Juvenile and Adult Rats," *Exp. Neurol.*, 154:231–240 (1998), which is hereby incorporated in its entirety).

The possibility that glioma implants modulate the expression of glutamate transporters in host cells was also considered. Immunohistochemical analysis of four-day-old glioma implants revealed that the expression of GLT1, an astrocytic glutamate transporter, was increased (~30–50% increase in labeling intensity) in the immediate vicinity of C6Glu$^+$ tumors, but not around C6Glu$^-$ and C6WT cell implants, but not detectable in C6Glu$^+$ tumors in accordance with the pattern of expression in cultured cells (FIG. 5E). The GLAST protein was only weakly expressed in host striata as earlier reported (Rothstein et al., "Localization of Neuronal and Glial Glutamate Transporters," *Neuron*, 13:713–725 (1994) which is hereby incorporated in its entirety). The upregulation of the GLT1 transporter around C6Glu$^+$ tumors might represent an adaptive response to a chronic load of glutamate.

Example 13

Memantine Limits Growth of RG2Glu$^+$ and C6Glu$^+$ gliomas

Figure 6:
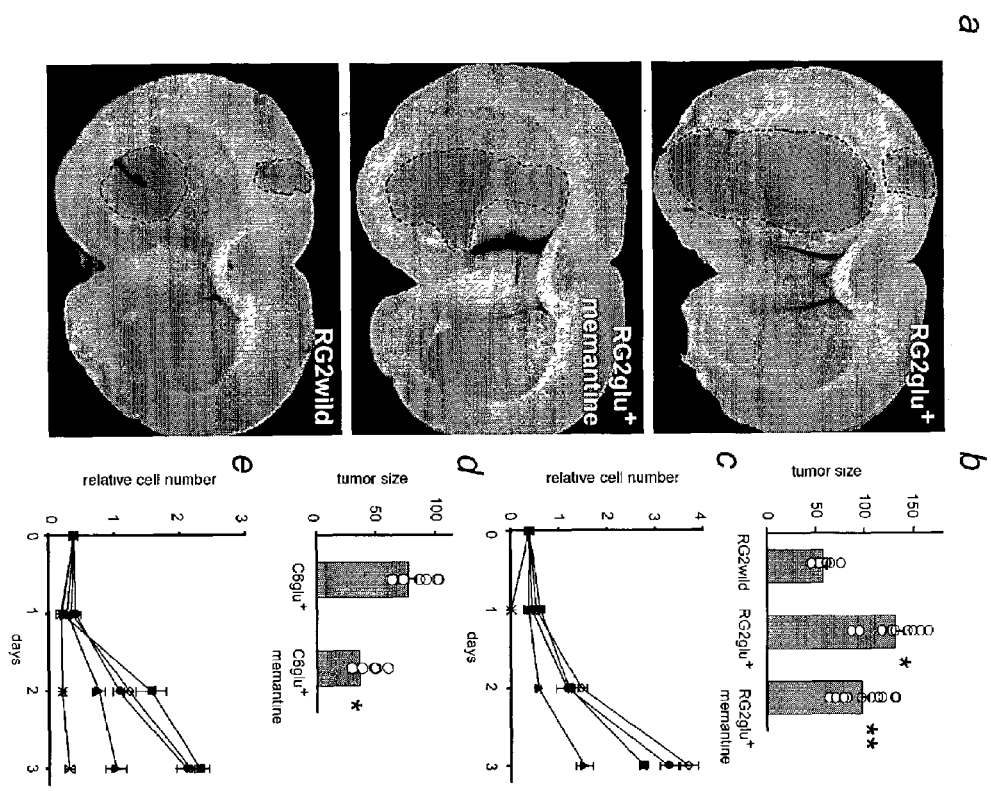
FIGS. 6A–E show memantine reduces the expansion of glutamate-secreting gliomas.

Rat C6 glioma is a cell line originally derived by injection of N-ethyl-N-nitrosourea in an outbred Wistar rat, so implantation in Wistar rats might evoke an immune response (Barth, R. F., "Rat Brain Tumor Models in Experimental Neuro-Oncology: The 9L, 6C, T9, F98, RG2 (D74), RT-2 and CNS-1 Gliomas," *J. Neurooncol.*, 36:91–102 (1998), which is hereby incorporated in its entirety). To broaden the observation that glutamate-secreting gliomas possess a growth advantage in situ, the effect of glutamate release from RG2 glioma cells after implantation in their syngeneic host, Fischer rats, was studied. Subcloning of RG2 produced several clones with high glutamate release compared with RG2 wild-type (RG2WT) cells. One of these glutamate-secreting clones, N144 (RG2Glu$^+$ cell) displayed a proliferation rate similar to wild type, but its glutamate release was increased two-fold. Intrastriate tumors of RG2Glu$^+$ cells expanded significantly faster than RG2WT implants, supporting the notion that glutamate secretion facilitates tumor expansion (FIGS. 6A–B). Importantly, RG2Glu$^+$ cell implants responded by a highly significant decrease in tumor volume, if host rats were treated with the uncompetitive NMDA receptor antagonist, memantine (25 mg/kg twice daily, i.p.). Tumor volume in memantine-treated rats was 26% smaller than vehicle-treated rats with RG2Glu$^+$ implants. Memantine is an NMDA antagonist structurally unrelated to MK801 and is presently in clinical use (Jain, K. K., "Evaluation of Memantine for Neuroprotection in Dementia," *Expert Opin. Investig. Drugs*, 9:1397–1406 (2000); Parsons et al., "Memantine is a Clinically Well Tolerated N-methyl-D-aspartate (NMDA) Receptor Antagonist—a Review of Preclinical Data," *Neuropharmacology*, 38:735–767 (1999), which are hereby incorporated in their entirety). Interestingly, memantine also effectively restricted the growth of C6Glu$^+$ tumors (FIG. 6D). Memantine did not reduce proliferation of cultured C6Glu$^+$ cells or RG2 glioma cells at low concentrations, but a significant reduction in proliferation of both cell types occurred if the concentration of memantine was raised to 100 μM or higher (FIGS. 6C–E). Because microdialysis studies have shown that administration of 25 mg/kg memantine i.p. resulted in peak concentrations of 1–2 μM in the central nervous system (CNS) (Danysz et al., "Aminoadamantanes as NMDA Receptor Antagonists and Antiparkinsonian Agents—Preclinical Studies," *Neurosci. Biobehav. Rev.*, 21:455–468 (1997), which is hereby incorporated in its entirety), it is unlikely that memantine directly reduced the growth of the implanted glioma cells. Collectively, these observations further strengthen the central role of NMDA receptor activation in the growth advantage of glutamate-secreting tumors.

Glutamate secreting glioma cells have a distinct growth advantage. The efficacy of MK801 and memantine in slowing tumor expansion, combined with the high frequency of neuronal apoptosis near C6Glu$^+$ tumors indicates that glutamate-dependent neurotoxicity facilitates tumor progression. Although the basis for this glutamate-associated growth advantage is unclear, the inflammatory response that accompanies excitotoxic neuronal degeneration might provide a favorable environment for tumor expansion (Scali et al. *Eur J Neurosci* 12:1900–1912 (2000); Bolton, S., and Perry, V. *Exp Neurol* 154:231–240 (1998), which are hereby incorporated by reference in their entirety). Tissue injury caused by X-ray irradiation, chemical exposure of mechanical trauma accelerates tumor progression (Fisher, B. et al. *Cancer* 20:23–30 (1967), which is hereby incorporated by reference in its entirety), in contrast to immune responses directed against the tumor, which instead reduce expansion (Graf, M. et al. *J Immunol* 163:5544–5551 (1999), which is hereby incorporated by reference in its entirety). C6Glu$^+$ gliomas evoked a local inflammatory response—as shown by the dense tissue infiltration of ED1$^+$ microglia cells/brain macrophages around implanted C6Glu$^+$ cells—whereas only occasional ED1 immunoreactivity occurred around tumors composed of C6Glu$^-$ cells.

These studies indicate that glutamate-secreting gliomas might stimulate inflammation and facilitate their own expansion in a paracrine fashion involving neuronal degeneration. In addition to the release of glutamate from glioma cells, both glutamate secreted from activated microglia and tumor-associated permeability changes of the blood-brain barrier might also contribute to further increases in the extracellular glutamate (Piani, D. et al. *Neurosci Lett* 133:159–162 (1991), which is hereby incorporated by reference in its entirety). However, these increases are counteracted by the highly efficient glutamate transporter expressed by both astrocytes and neurons (Rothstein, J. D. et al. *Neuron* 16:675–686 (1996); Anderson, C. M. & Swanson, R. A. *Glia* 32:1–14 (2000); Swanson, R. et al. *J Neurosci* 17:932–940 (1997), which are hereby incorporated by reference in their entirety). Due to the high glutamate release, epileptic seizures are a common symptom in patients with malignant gliomas, and the commonly used anticonvulsants are often ineffective (Moots, P. L. et al. *Arch Neurol* 52:717–24 (1995); Pace, A. et al. *J Exp Clin Cancer Res* 17:479–482 (1998), which are hereby incorporated by reference in their entirety). For these considerations, anticonvulsants targeting glutamate receptors might prove more effective than their GABAergic counterparst in the treatment of malignant gliomas.

Glutamate excitocity is involved in numerous CNS disorders, including acute pathologies of stroke and head trauma, as well as in the long-term progressive neuronal loss in ALS, Huntington's Disease, Alzheimer's Disease, epilepsia, and in immune-mediated damage in multiple sclerosis (McDonald, J. et al. *Nat Med* 4:291–297 (1998); Meldrum, B. S. *J Nutr* 130:1007S-1015S (2000); Smith, T. et al. *Nat Med* 6:62–66 (2000), which are hereby incorporated by reference in their entirety). Although drugs that antagonize glutamate receptors are consistently neuroprotective in experimental animal models, the therapeutic potential of NMDA receptor antagonists in stroke and traumatic brain injury has been complicated by neurological side-effects (Meldrum, B. *J Nutr* 130:1007S-1015S (2000), which is hereby incorporated by reference in its entirety). However, it is important to note that excitotoxic neuronal injury in ischemia and head trauma results from 50–200-fold transient increases in the extracellular content of glutamate (Lipton, P. *Physiol Rev* 79:1431–1568 (1999), which is hereby incorporated by reference in its entirety). The modest degree of elevation of glutamate in tumor implants is comparable to these reported in glioma implants (using microdialysis: Behrens, P. et al. *J Neurooncol* 47:11–22 (2000), which is hereby incorporated by reference in its entirety), dementia (Harkany, T. et al. *Eur J Neurosci* 12:2735–2745 (2000), which is hereby incorporated by reference in its entirety) and in spontaneous epileptic Wistar rats (Kanda, T. et al. *Life Sci* 59:1607–1616 (1996), which is hereby incorporated by reference in its entirety). The chronic nature of glutamate release in these cases might suffice to mediate neuronal degeneration. In this regard, memantine has been administered for prolonged periods in patients with Parkinson's Disease, dementia, and spasticity with few side effects (Jain, K. *Expert Opin Investig Drugs* 9:1397–1406 (2000); Parsons, C. et al. *Neuropharmacology* 38:735–767 (1999); Danysz, W. et al. *Neurosci Biobebav Rev* 21:455–468 (1997), which are hereby incorporated by reference in their entirety). The present study indicates that inhibition of glioma glutamate release or blockade of glutamate receptors may serve as an effective strategy for the treatment of patients with malignant glioma.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating glioblastoma in a subject comprising:
   providing a NMDA receptor antagonist, wherein the NMDA receptor antagonist is selected from the group consisting of memantine and MK801 and
   administering the NMDA receptor antagonist to a subject with a glioblastoma under conditions effective to treat the glioblastoma and prevent spread of tumor cells, wherein the NMDA receptor antagonist is administered at a dose lower than that at which glutamate antagonists cause direct cytotoxicity.

2. The method according to claim 1, wherein said glioblastoma is located in the brain of the subject.

3. The method according to claim 1, wherein said glioblastoma is located in the spinal cord of the subject.

4. The method according to claim 1, wherein said glioblastoma is malignant.

5. The method according to claim 1, wherein said glioblastoma is benign.

6. The method according to claim 1, wherein said NMDA receptor antagonist is MK801.

7. The method according to claim 1, wherein said NMDA receptor antagonist is memantine.

8. The method according to claim 1, wherein the subject is a mammal.

9. The method according to claim 8, wherein the mammal is a human subject.

10. The method according to claim 8, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

11. The method according to claim 1, wherein said NMDA receptor antagonist is present in a pharmaceutical composition comprising the NMDA receptor antagonist and a pharmaceutically-acceptable carrier.

* * * * *